United States Patent [19]

Fréchette et al.

[11] Patent Number: 5,064,645

[45] Date of Patent: Nov. 12, 1991

[54] **HYPERIMMUNE COMPOSITION FOR PASSIVE IMMUNIZATION OF FISHES AGAINST FURUNCULOSIS CAUSED BY *AEROMONAS SALMONICIDA***

[75] Inventors: Jean-Louis Fréchette; Youssef Elazhary, both of St-Hyacinthe, Canada

[73] Assignee: Pisciconsult Developpement Inc., Canada

[21] Appl. No.: 558,599

[22] Filed: Jul. 27, 1990

[51] Int. Cl.$^5$ .................... A61K 39/00; A61K 39/02; A61K 35/14

[52] U.S. Cl. .................... 424/85.8; 424/92; 424/531; 530/387; 530/388

[58] Field of Search .................... 424/92, 85.8, 531; 530/387, 388

[56] References Cited

U.S. PATENT DOCUMENTS 4,223,014  9/1980  Garrison et al. .................... 424/92

FOREIGN PATENT DOCUMENTS 915086  11/1972  Canada .

OTHER PUBLICATIONS

Ellis et al. Chem. Absts. 109 (11) 90872g.

*Primary Examiner*—Thurman K. Page
*Assistant Examiner*—G. S. Kishore
*Attorney, Agent, or Firm*—Dressler, Goldsmith, Shore, Sutker & Milnamow, Ltd.

[57] ABSTRACT

The present invention relates to a serum for passive immunization of fish against furunculosis caused by *Aeromonas salmonicida*, which comprises antibodies against *A. salmonicida* isolated from fish naturally infected with furunculosis in an intraperitoneal injectable carrier. There is also provided a method for preparing a serum for passive immunization of fish against furunculosis caused by *Aeromonas salmonicida*, comprising the steps of: a) administering to a mammal selected from the group consisting of bovine, ovine, caprine and equine a sufficient amount of *A. salmonicida* to produce antibodies; b) collecting from the mammal the serum containing the antibodies against *A. salmonicida*; c) precipitating and purifying said antibodies by a single precipitation step with an aqueous ammonium sulphate solution in a concentration of about 40% weight/volume and separating the purified precipitated antibodies; d) lyophilizing the purified antibodies; and e) reconstituting the lyophilized antibodies of step d) at about 5 to 7×concentration in an intraperitoneal injectable carrier.

3 Claims, No Drawings

HYPERIMMUNE COMPOSITION FOR PASSIVE IMMUNIZATION OF FISHES AGAINST FURUNCULOSIS CAUSED BY AEROMONAS SALMONICIDA

BACKGROUND OF THE INVENTION

Epidemics of bacterial diseases are common in natural water streams and cultured fish populations. Predisposition to such outbreaks frequently is associated with poor water quality, organic loading of the aquatic environment, handling and transport of fish, marked temperature changes, hypoxia, and related stressful conditions. High concentrations of water-borne bacteria are normally found in ponds and aquaria. Many of these aquatic bacteria are opportunistic, facultative pathogens, being activated by an adverse environment or a debilitated host.

Aeromonas salmonicida is a gram-negative, non-motile, pigment-producing rod originally described as the cause of a septicemic disease of salmonid fish (furunculosis). It is also a serious pathogen of many other freshwater and marine fish and may produce high morbidity and mortality. In the acute form of the disease, hemorrhages are found in the fins, tail, muscles, gills, and internal organs. In more chronic forms, focal areas of swelling, hemorrhage, and tissue necrosis develop in the muscles. These lesions progress to crateriform abscesses discharging from the skin surface (furuncles). Carrier fish show no clinical signs of the disease while they are the ones which disseminate the disease to other populations of fish.

Aeromonas salmonicida, the bacterium responsible for furunculosis in fish, continues to be the cause of serious losses in cultured salmonids, and, despite the fact that some 40 years have elapsed since efforts were first undertaken to develop a vaccine to control the disease (Duff D. C. B., J. of Immunology, 1942, 44:87-94), a proven, mass-administered, anti-furunculosis vaccine without any latent period is still lacking. At the present time, the vaccine on the market does not give a good immunization and requires a long period of time before the active immunization takes place.

Avoidance is the most effective prevention since A. salmonicida is an obligatory fish pathogen. Fish and fish eggs should be obtained from sources known to be free of the disease. Infected stocks should be depopulated and wild-fish reservoirs eliminated.

A regular vaccine requires a latent period in order to be effective in protecting the administered patient, during which the patient's immune system is developing the antibodies and lymphocytes which would recognize the disease-causing agent.

Canadian Patent 915,086 discloses an antigenic composition useful for oral immunization of salmonids against furunculosis disease, a method of preparing the antigen and a method for administering the antigenic composition to fish. This oral immunization does not provide an immediate protection against furunculosis infection caused by A. salmonicida. The antigenic material administered in feed requires a latent period for the fish's immune system to provide an efficient protection against the infection.

According to the report of Aqua Health, a vaccine is usually efficient after a period of about 40 days at a temperature of around 10° to 12° C. and may require an even longer period if the temperature is lower than 10° C. (AQUA HEALTH LIMITED, 1987, Report on Vibrio anguillarum and Aeromonas salmonicida, Charlottetown, P.E.I., Canada). This important delay between the administration of the vaccine and the appearance of immunity for the disease, may cause the stress of the administration itself to promote the disease before the fish are appropriately immunized (TURGEON Y., 1985, Report of 'Ministère du Loisir, de la Chasse et de la Pêche', Quebec).

The antibacterial therapy, using antibiotics, provides to the fish an immediate protection against the infectious bacteria, but it inevitably results in a second generation of bacteria which is resistant to this antibacterial treatment. Even if this treatment has the advantage of procuring to the fish an instant protection against the pathogenic bacteria, the subsequent antibacterial treatment becomes complicated by the bacteria-inherited resistance. The use of antibiotics also requires a delay period, which is sometimes very long, before human consumption is possible.

The best way to protect fish against A. salmonicida would be to have a product or a method which would combine the advantages of the antibacterial treatment with the advantages of the vaccine without having their respective disadvantages.

It would be highly desirable to have a means to effectively immunize fish against A. salmonicida for a considerably long period of time and without having a latent period wherein the fish are vulnerable.

Moreover, it would also be highly desirable to have a passive immunization means which would readily protect the fish against this bacteria upon their administration.

SUMMARY OF THE INVENTION

Surprisingly and in accordance with the present invention, there is provided a serum for passive immunization of the fish against furunculosis caused by Aeromonas salmonicida, which comprises antibodies against A. salmonicida isolated from fish naturally infected with furunculosis in an intraperitoneal injectable carrier.

There is provided in accordance with the present invention a method for preparing a serum for passive immunization of fish against furunculosis caused by Aeromonas salmonicida, comprising the steps of:

a) administering to a mammal selected from the group consisting of bovine, ovine, caprine and equine a sufficient amount of A. salmonicida to produce antibodies;

b) collecting from the mammal the serum containing the antibodies against A. salmonicida;

c) precipitating and purifying said antibodies by a single precipitation step with an aqueous ammonium sulphate solution in a concentration of about 40% weight/volume and separating the purified precipitated antibodies;

d) lyophilizing said purified precipitated antibodies; and e) reconstituting the lyophilized antibodies of step d) at about 5 to 7× concentration in an intraperitoneal injectable carrier.

In a further aspect of the invention, there is provided an improvement wherein antibodies against A. salmonicida are produced by administering to a mammal a sufficient amount of A. salmonicida and collected from the mammal serum which consists in precipitating and purifying said antibodies by a single precipitation step with an aqueous ammonium sulphate solution in a concentration of about 40% weight/volume and separating the purified precipitated antibodies; lyophilizing said purified precipitated antibodies; and reconstituting the lyophilized antibodies of step d) at about 5 to 7×concentration in an intraperitoneal injectable carrier.

Other advantages of the present invention will be readily illustrated by referring to the following description.

DETAILED DESCRIPTION OF THE INVENTION

Throughout the present application the following expressions are used:

| | |
|---|---|
| Challenge | Experimentally infecting fish. |
| Control | Fish which are experimentally infected (challenged) without receiving a prior or post treatment, they permit the evaluation of the quality of the challenge. |
| RPS | Relative Percentage of Survival which is calculated as follows: $$RPS = 100 \times \left(1 - \frac{\% \text{ of deaths in the vaccinated population}}{\% \text{ of deaths in the control population}}\right)$$ |
| Witness | Fish which are not submitted to the challenge nor to any treatment, they permit the evaluation of the stabulation conditions. |

The present invention relates to a serum for passive immunization of fish against furunculosis caused by *Aeromonas salmonicida*, which comprises antibodies against *A. salmonicida* isolated from fish naturally infected with furunculosis in an intraperitoneal injectable carrier.

The serum of the present invention is prepared according to the following general procedure:

a) administering to a mammal selected from the group consisting of bovine, ovine, caprine and equine a sufficient amount of *A. salmonicida* to produce antibodies;

b) collecting from the mammal the serum containing the antibodies against *A. salmonicida*;

c) precipitating and purifying said antibodies by a single precipitation step with an aqueous ammonium sulphate solution in a concentration of about 40% weight/volume and separating the purified precipitated antibodies;

d) lyophilizing said purified precipitated antibodies; and e) reconstituting the lyophilized antibodies of step d) at about 5 to 7×concentration in an intraperitoneal injectable carrier.

The serum of the present invention for fish is more preferably directed to salmonids but can also be administered to other fish which are succeptible of being infected with *A. salmonicida*.

A virulent *A. salmonicida* strain which was used as a reference in accordance with the present invention has been provided by Dr. Paterson which is currently working for Aqua Health (Connaught Laboratory, 1984, Toronto, Ontario); it is of the subspecies salmonicida and is identified as 84.

One preferred virulent *A. salmonicida* strain which was used in accordance with the present invention was isolated from a dead Atlantic salmon during a furunculosis epidemic which occurred at 'Gaspé' (Quebec, Canada); it is of the subspecies salmonicida and is identified as strain 1-83.

In accordance with the present invention, the following culture medium can be used:

Brain Heart Infusion ® agar (BHI, sold by Difco Laboratories);

Furunculosis ® agar (FA, sold by Difco Laboratories); and

Trypticase Soy ® agar (TSA, sold by Difco Laboratories) supplemented with 0.01% of Coomassie Blue R-250 ® (Evenberg D. R. V. et al., 1985, *Biochim. Biophys. ACTA*, 815:233–244).

CULTURE OF BACTERIA

Before being freezed in liquid nitrogen for long-term conservation, the bacteria culture is suspended in the following medium: 40 g of Dextran T-40 ®, 75 g of sucrose and 10 g of sodium glutamate in 1 L of water.

The master strains of *A. salmonicida* are cultivated separately in BHI at 16° C. for 24 hours and the resulting bacterial broth is inoculated onto FA medium for the obtention of isolated bacterial colonies. The inoculated FA medium is then incubated at 16° C. for 48 hours. An isolated colony is selected and inoculated in BHI for another 48 hours. The BHI is then centrifuged at 6000 rpm for 20 minutes. The bacterial cells are washed twice in the freezing medium and are then freezed or lyophilized.

PREPARATION OF THE VIRULENT BACTERIAL CULTURE OF THE STRAIN 1-83

1 mL of freezed or lyophilized bacteria strain 1-83 is used to inoculate 5 mL of BHI medium. This bacterial culture is incubated at 16° C. for 72 hours. The resulting broth is then transferred into 20 mL of BHI medium and incubated at 16° C. for 48 hours. This preculture is then transferred into 1 L of BHI medium and incubated at 16° C. for 72 hours.

The absence of any bacterial contamination is verified by the inoculation of three FA agar which are respectively incubated at 16° C., 30° C. and 37° C. for 4 days each. The specific characteristics of each infectious *A. salmonicida* strains are determined by the inoculation of Trypticase Soy ® agar medium (TSA, sold by Difco Laboratories) supplemented with 0.01% of Coomassie Blue R-250 ® (Evenberg D. R. V. et al., 1985, *Biochim. Biophys.* ACTA, 815:233-244) and incubated at 17° C. for 36 hours.

PREPARATION OF THE NON-VIRULENT BACTERIAL CULTURE OF THE STRAIN 1-83

Because of the autoagglutination and of the non-autoagglutination characteristic of the virulent versus the non-virulent strain, the agglutination test is performed using the non-virulent strain as an antigenic material. In order to isolate the non-virulent strain, an FA medium is inoculated with strain 1-83 and incubated at 30° C. for 72 hours. Ishiguro E. E. et al (1981, *J. Bacterial.* 148:333-340) have demonstrated that at a temperature of 30° C., only non-virulent mutants can grow. The resulting mutant colonies are then inoculated on FA medium and incubated at 30° C. for 48 hours. This culture is kept at 4° C. and reincubated at every three weeks.

MAMMAL

The mammal which can be administered a sufficient amount of *Aeromonas salmonicida* to produce antibodies in accordance with the present invention can be selected from the group consisting of bovine, ovine, caprine and equine.

One preferred mammal which is used in accordance with the present invention is a cow and more specifically of the species Holstein. The cows used for the serum production were negative for bovine leucosis as well as for bovine virus diarrhea (BVD).

EXAMPLE I

Production of serum

*A. salmonicida* bacterial cultures of virulent Quebec strain 1-83 are prepared as described previously. For the production of the hyperimmune serum of the present invention, animals are injected with 1-83 bacterial cultures without any prior washing nor any suspension in phosphate buffer saline (PBS).

An emulsion is prepared by mixing equal quantities of incomplete Freund adjuvant (sold by Difco) and of the PBS bacterial suspension.

Two cows are each intramuscularly injected with 20 mL of bacterial emulsion which contains 10 mL of PBS bacterial suspension and 10 mL of the incomplete Freund adjuvant for days 1, 2 and 3 of the first week; for the second and third week on day 1 the animals received 20 mL of the same bacterial emulsion and for days 2 and 3 only the PBS bacterial suspension was used (without any incomplete Freund adjuvant).

Ten days after the last injection, blood is withdrawn from the cows, then it is kept at 37° C. for one hour and at 4° C. for 20 hours. The blood is then centrifuged at 8000 xg for 30 minutes at 4° C.

Purification of IgG

Each aliquot of serum containing IgG is diluted 3 times with PBS (1 L of serum with 2 L of PBS) and 2 L of saturated ammonium sulfate of pH 7.2 is added to obtain a final concentration of 40% weight/volume of ammonium sulfate at room temperature while continuously shaking with a magnetic stirrer. Thirty minutes later, the solution is centrifuged at 1000 xg for 15 minutes and the precipitate is washed with a 40% weight/volume of ammonium sulfate solution.

The precipitate is dissolved in PBS and the insoluble material is removed by a centrifugation. The precipitated IgG is dissolved in PBS and dialyzed overnight against 500 mL of PBS at 4° C.

This is a one-step precipitation and the washing is just a performed to enhance the purity of the collected IgG. It was discovered that this single-step precipitation unexpectedly produces purified antibodies which are surprisingly of a higher immunological quality than the antibodies obtained by a two-steps precipitation.

Concentration of the serum by lyophilization

The purified IgG against *Aeromonas salmonicida* were concentrated by freeze drying into a powder form. The serum is then suspended in a quantity of water (a liquid intraperitoneal injectable carrier), according to a desired end concentration which ranges between 5 to 7×.

EXAMPLE II

Hyperimmune non-lyophilized non-concentrated serum

This experiment consisted primarily of administering the serum of the present invention to fish prior to the challenge in order to determine the safety and the duration of the immunity.

Material and Methods

Fish were stalled in Swedish type tanks and finally they were kept in transfer tanks. These tanks are made of fiberglass and are thermostatic. Each tank comprises four compartments of 2,700 L. The water was not changed during the experiment and the oxygenation was provided with compressed air diffusion. The water temperature varied between 10.0° C. and 12.5° C. during the experiment.

Fish were fed ad libitum in granulated form, three times a day for the period prior to the challenge and twice a day after the challenge.

After the challenge, the dead fish were collected twice a day during a period of eleven days and these fish were then subjected to a bacteriological examination.

The fish with or without external signs of furunculosis were opened according to the usual bacteriological process. Samples taken from kidneys were cultivated in parallel on FA and TSA medium which were incubated during three days at 16° C. The bacterial cultures were tested according to the standard procedure of "Fishing and Oceans of Canada" (Rules on Health Protection of Fish, Guide of Procedures).

Fish

Seven hundred (700) Atlantic salmons, which all came from the pisciculture of 'l'Anse-Pleureuse' in 'Gaspésie' (Quebec), were used during the experiment.

Four hundred and sixty (460) of these fish were of the 'Cascapédia 85' lot and were transported in plastic bags filled with pure oxygen to the pisciculture of Tadoussac (lots 1 to 11). These fish were previously vaccinated by immersion (Furogen b ®, Aqua Health Limited, Charlottetown, P.E.I., Canada) against furunculosis in April 1986.

The other two hundred and forty (240) fish were transported in tanker from the pisciculture 'l'Anse-Pleureuse' to the experimental site. These fish were taken from the 'Sainte-Anne' lot and had never been vaccinated (lots 12 to 15).

Experimental protocol

Two hundred and ninety five (295) fish were injected at the time mentioned in Table I. Three hundred and fifty three (353) fish served as control challenged and fifty-two (52) fish served as control non-challenged.

The serum dosage was 8.0 mL/kg per weight in a solution suitable for injection of 0.2 mL/fish which was administered by intraperitoneal injection. The serum used had been previously frozen with the exception of lot 6 which had been previously lyophilized. The fish weight was determined through sampling and the dosage had been calculated for the average weight. The fish were transported at the experimental site the same day they were submitted to the challeng.

TABLE I

| | Experimental protocol | | | | |
|---|---|---|---|---|---|
| Date of No. serum injection[1] | No. of days from challenge before | after | No. of fish | Source[2] | Lot |
| 07-08-86 | 53 | — | 57 | Cascapedia | 1 |
| 07-24-86 | 37 | — | 31 | Cascapedia | 2 |
| 07-24-86 | 37 | — | 29 | Cascapedia | 3 |
| 08-07-86 | 23 | — | 37 | Cascapedia | 4 |

TABLE I-continued

Experimental protocol

| Date of No. serum injection[1] | No. of days from challenge before | No. of days from challenge after | No. of fish | Source[2] | Lot |
|---|---|---|---|---|---|
| 08-19-86 | 11 | — | 38 | Cascapedia | 5 |
| 08-19-86 | 11 | — | 32 | Cascapedia | 6 |
| 08-30-86 | 0 | — | 22 | Cascapedia | 7 |
| 08-30-86 |  | — | 23 | Cascapedia | 8 |
| 09-03-86 |  | 4 | 26 | Cascapedia | 10 |
| Control |  |  | 113 | Cascapedia | 9 |
|  |  |  | 60 | Sainte-Anne | 12 |
|  |  |  | 60 | Sainte-Anne | 13 |
|  |  |  | 60 | Sainte-Anne | 14 |
|  |  |  | 60 | Sainte-Anne | 15 |
| Witness |  |  | 52 | Cascapedia | 11 |

[1]The serum was frozen for its preservation with the exception of lot #6 which was lyophilized.
[2]The fish from 'Cascapedia' were previously vaccinated with the Aqua Health vaccine and the fish from 'Sainte-Anne' were not vaccinated.

CHALLENGE

The group of fish submitted to the challenged (Table II) were infected by an immersion of 60 seconds in 1 L of a bacterial suspension of *A. salmonicida* ($1 \times 10^9$ cells/mL).

TABLE II

Passive immunity of the Atlantic salmon

| Treatment | Number of days | Number of Fish | Death no. | Death % | Relative Survival % |
|---|---|---|---|---|---|
| immunized before the challenge | 53 | 57 | 24 | 42.1 | 56.0 |
|  | 37 | 31 | 0 | 0 | 100.0 |
|  |  | 29 | 0 | 0 | 100.0 |
|  | 23 | 37 | 2 | 5.4 | 94.5 |
|  | 11 | 38 | 2 | 5.3 | 94.4 |
|  |  | 32* | 2* | 6.2* | 93.5* |
|  | 0 | 22 | 4 | 18.2 | 81.0 |
|  |  | 23 | 10 | 43.5 | 54.5 |
| immunized after the challenge | 4 | 26 | 26 | 100.0 | 0 |
| Control (challenged) |  | 353 | 343 | 97.2 |  |
| Witness (non-challenged) |  | 52 | 0 | 0 |  |

*This serum was lyophilized while the others were frozen for their preservation.

Results

Witness (non-challenged)

During the experiment, none of these fish died. This demonstrate that the stalling conditions were excellent and cannot be a cause of fish death.

Control (challenged)

Eleven days after the challenge, the death rate was of 93.8% for the vaccinated lot (vaccinated with Furogen b ®, Aqua Health Ltd.) and varied between 96.7% and 100% for the non-vaccinated lot (Table III). These results demonstrate that the challenge was efficient in killing fish.

TABLE III

Death in number and percentage following the challenge

| Lot (challenged) | No. of fish | Number of days after the challenge |  |  |  |  |  |  |  |  |
|---|---|---|---|---|---|---|---|---|---|---|
|  |  | 3 | 4 | 5 | 6 | 7 | 8 | 9 | 10 | 11 |
| Not vaccinated |
| 12 | 60 | 0 | 9 | 21 | 22 | 6 | 0 | 1 | 0 |  |
|  | % dead |  | 15 | 50 | 86.7 | 96.7 | 96.7 | 98.3 |  |  |
| 13 | 60 | 0 | 11 | 26 | 14 | 7 | 0 | 0 | 0 |  |
|  | % dead |  | 18.3 | 61.7 | 85.0 | 96.7 |  |  |  |  |
| 14 | 60 | 0 | 14 | 20 | 20 | 4 | 0 | 1 | 1 |  |
|  | % dead |  | 23.3 | 56.7 | 90.0 | 96.7 | 96.7 | 98.3 | 100.0 |  |
| 15 | 60 | 0 | 9 | 26 | 11 | 11 | 0 | 0 | 1 | 2 |
| % | % dead |  | 15 | 58.3 | 76.7 | 95.0 | 95.0 | 95.0 | 96.7 | 100 |
| TOTAL | 240 | 0 | 43 | 93 | 67 | 28 | 0 | 2 | 2 | 2 |
|  | % dead |  | 17.9 | 56.7 | 84.6 | 96.2 | 96.2 | 97.1 | 97.9 | 98.7 |
| Vaccinated with bacteria (Aqua Health) |
| 9 | 113 | 1 | 20 | 36 | 22 | 14 | 8 | 3 | 1 | 1 |
|  | % dead | 0.9 | 18.6 | 50.4 | 69.9 | 82.3 | 89.4 | 92.0 | 92.9 | 93.8 |
| TOTAL | 353 | 1 | 63 | 129 | 89 | 42 | 8 | 5 | 3 | 3 |
|  | % dead | 0.3 | 18.1 | 54.7 | 79.9 | 91.8 | 94.0 | 95.5 | 96.3 | 97.2 |

Passive immunity of the hyperimmune serum

Table II shows that between 93.5 and 100% of the fish which received the serum 11 to 37 days before the challenge survived the latter. When the serum is administered on the same day as the challenge, the average protection is of 67.5% (81.0% + 54.5%/2). There is observed no significant difference of protection provided between the serum which is previously frozen and the serum which is previously lyophilized.

EXAMPLE III

Concentrated lyophilized hyperimmune serum

This experiment consisted primarily of determining the safety and duration of this serum for passive immunity of fish using salmons and speckled trouts.

Material and Methods

Fish were stalled in Swedish type tanks under the same environmental conditions as described in Example II. The water temperature varied between 13.2° C. and 19.2° C. during the experiment.

Fish were fed ad libitum in granulated form, three times a day for the period prior to the challenge and twice a day after the challenge.

Fish

Salmon

Two hundreds and sixty (260) Atlantic salmons, which all came from the pisciculture of 'l'Anse-Pleureuse' in 'Gaspésie' (Quebec), were used during the experiment.

Trout

Forty three (43) speckled trouts, which came from lot 87 at the pisciculture of 'F. E. Fortin' in 'La Tuque' (Quebec, Canada), were transfered in 1987 at the pisciculture in 'St-Faustin' (Quebec, Canada).

Experimental protocol

Salmon

One hundred and fifty three (153) fish were injected with the serum. Fifty five (55) fish served as control challenged and fifty two (52) fish served as control non-challenged.

Trout

Twenty two (22) fish were injected with the serum. Ten (10) fish served as control challenged and eleven (11) fish served as control non-challenged.

Challenge

The group of fish submitted to the challenge were infected by an immersion of 60 seconds in 1 L of a bacterial suspension of *A. salmonicida* ($1 \times 10^9$ cells/mL) and were then transfered to their experimental tanks without any washing.

Results

Witness (non-challenged)

Salmon: During the expeiment, none of these fish died.
Trout: During the experiment, none of these fish died.
This demonstrates that the stalling conditions were excellent and cannot be a cause of fish death.

Control (challenged)

Salmon: Eleven days after the challenge, the death rate was of 87.3%.
Trout: Eleven days after the challenge, the death rate was of 90%
This demonstrate that the challenge was efficient.

Passive immunity

Salmon

The fish which received the serum 121 days prior to the challenge had a relative survival percentage of 69.6%, whereas the fish which received the serum 87 days prior to the challenge had a relative survival percentage of 91.6% (Table V).

Trout

The trouts which received the serum 34 days prior to the challenge gave the results shown in Table IV.

Lot #1 consisted of 12 trouts which were in good health until the oxygenating system broke down causing their death. These dead trouts gave a negative bacteriological results.

Lot #2 consisted of 10 trouts among which only one died. The dead fish also gave a negative bacteriological result.

TABLE IV

| Passive immunity of trouts using the hyperimmune serum | | | |
|---|---|---|---|
| Number of days after the immunization | No. of Fish | Death % | Relative Survival % |
| 34 | lot #1:12 | 0*% | 100 |
| 34 | lot #2:10 | 10**% | 88.9 |
| Control (challenged) | 10 | 90% | 10 |
| Witness (non-challenged) | 11 | 0% | 100 |

*The fish of lot 12 died on the seventh day pursuant to the challenge due to a stop of the oxygenating system.
**One trout had a marked ""exophtalmie"" without any sign of furunculosis, which turned out to be negative for furunculosis in a bacteriological test.

The serum dosage was 0.4 mL/kg per weight in a solution suitable for injection which was administered by intraperitoneal injection.

TABLE V

| Passive immunity of salmons using the hyperimmune serum | | | | |
|---|---|---|---|---|
| Number of days after the immunization | No. of Fish | Death no. | Death % | Relative Survival % |
| 121 | 98 (treated) | 26 | 26.5 | 69.6 |
| 87 | 55 (treated) | 4 | 7.3 | 91.6 |
| Control (non-challenged) | 55 | 48 | 87.3 | |
| Witness (challenged) | 52 | 0 | 0 | |

What is claimed is:

1. A composition for passive immunization of fish against furunculosis caused by *Aeromonas salmonicida*, comprising mammal immunoglobulins G specific to *A. salmonicida* in an aqueous solution.

2. The composition according to claim 1, wherein said mammal immunoglobulins G is at a concentration between 25 to 30 mg/ml.

3. The composition according to claim 1, wherein said mammal immunoglobulins G are polyclonal mammal immunoglobulins G.

* * * * *